United States Patent
Reekie

[11] Patent Number: 6,105,218
[45] Date of Patent: Aug. 22, 2000

[54] SNAP-TYPE FASTENING DEVICE

[75] Inventor: George Reekie, Salem, Mass.

[73] Assignee: Siemens Medical Systems, Inc., Iselin, N.J.

[21] Appl. No.: 09/212,887

[22] Filed: Dec. 16, 1998

[51] Int. Cl.[7] .................................................. F16B 7/04
[52] U.S. Cl. ............................... 24/518; 24/339; 24/543; 24/115 R; 403/396; 403/397
[58] Field of Search ........................... 24/517, 518, 511, 24/459, 543, 339, 115 R, 115 H, 489, 335, 329, 16 R, 19, 270; 248/68.1, 74.2, 74.3; 403/344, 391, 396, 397, 389, 385; 604/174; 128/DIG. 26

[56] References Cited

U.S. PATENT DOCUMENTS

| | | | |
|---|---|---|---|
| 3,809,371 | 5/1974 | Martini | 256/47 |
| 4,118,838 | 10/1978 | Schiefer et al. | 24/115 R |
| 4,308,642 | 1/1982 | Heyman | 24/306 |
| 4,771,516 | 9/1988 | Foth | 403/396 X |
| 4,971,271 | 11/1990 | Sularz | 248/68.1 |
| 5,459,903 | 10/1995 | Treacy | 24/3.13 |
| 5,494,245 | 2/1996 | Suzuki et al. | 248/74.1 |
| 5,535,969 | 7/1996 | Duffy, Jr. | 248/68.1 |
| 5,572,776 | 11/1996 | Murphy et al. | 24/543 |
| 5,703,330 | 12/1997 | Kujawski | 24/339 X |
| 5,820,048 | 10/1998 | Shereyk et al. | 248/68.1 |
| 5,937,488 | 8/1999 | Geiger | 24/339 |

FOREIGN PATENT DOCUMENTS 0 572 684   7/1996   European Pat. Off. .

*Primary Examiner*—Anthony Knight
*Assistant Examiner*—Robert J. Sandy
*Attorney, Agent, or Firm*—Lawrence C. Edelman

[57] ABSTRACT

A fastener comprising first and second separable members, for engaging an elongate element. Each member includes first and second complementary shaped partial-cylindrical portions formed on a facing side thereof. The first and second partial-cylindrical portions of the first member have outside dimensions that are complementarily dimensioned with respect to the inside dimensions of the first and second partial-cylindrical portions of the second member, so that the first and second partial-cylindrical portions of the first member selectively engage and nest within the first and second partial-cylindrical portions of the second member when the facing side of the first and second members are positioned towards each other. The elongate element is engaged between the first and second members of the fastener by an engagement area formed when one of the first and second partial-cylindrical portions are nested.

10 Claims, 3 Drawing Sheets

SNAP-TYPE FASTENING DEVICE

BACKGROUND OF THE INVENTION

1. Field of the Invention

The invention relates to fastening devices, and more particularly to a snap type fastener for securing elongate or tubular elements.

2. Description of the Prior Art

The use of various devices for joining medical tubes and cables to a medical patient is well known in the medical arts. A representative one of many devices which facilitate such a joining is described in U.S. Pat. No. 4,308,642. The device comprises a generally rectangular pad having a "fuzzy fiber" (i.e., VELCRO®) gripping area for securing one or more elongate elements thereon, and an alligator-clip type of clamp at one end of the rectangular pad. During use, one or more elongate elements required to be joined with a patient are tightly secured onto the pad using the gripper area, and the assembly is then secured near the patient in order to support and relieve the strain of the elongate elements that are connected to the patient. The securing of the assembly is accomplished, for example, by engaging the bed sheet or gown of the patient between the jaws of the clip. Generally, the elongate elements comprise electrical cables and/or tubular members, such as required for monitoring physiological parameters of the patient, i.e., for monitoring the electrical heart activity (EKG) or blood pressure of the patient.

The use of a fuzzy fiber pad is generally undesirable from a cleanliness point of view due to the many small recesses that exist in the fibers, and a toothed metal clip is also undesirable due to the possibility of injury to the patient, rusting of the metal parts, and damaging of the medical tubes or cables.

It would be desirable to provide a device which can be easily operable using only one hand, to selectively secure elongate members that are joined with the patient to a variety of different types of supports (such as a bed sheet, hospital gown), in a non-obtrusive manner. It would be also be desirable for such a device to be easily manufactured use non-rusting parts, as well as parts that are easy to clean and are reusable a number of times without adversely affecting its operability.

SUMMARY OF THE INVENTION

A fastener comprising first and second separable members, for engaging an elongate element. Each member includes first and second complementary shaped partial-cylindrical portions formed on a facing side thereof. The first and second partial-cylindrical portions of the first member have outside dimensions that are complementarily dimensioned with respect to the inside dimensions of the first and second partial-cylindrical portions of the second member, so that the first and second partial-cylindrical portions of the first member selectively engage and nest within the first and second partial-cylindrical portions of the second member when the facing side of the first and second members are positioned towards each other. The elongate element is engaged between the first and second members of the fastener by an engagement area formed when one of the first and second partial-cylindrical portions are nested.

DETAILED DESCRIPTION OF THE INVENTION

Figure 1A:
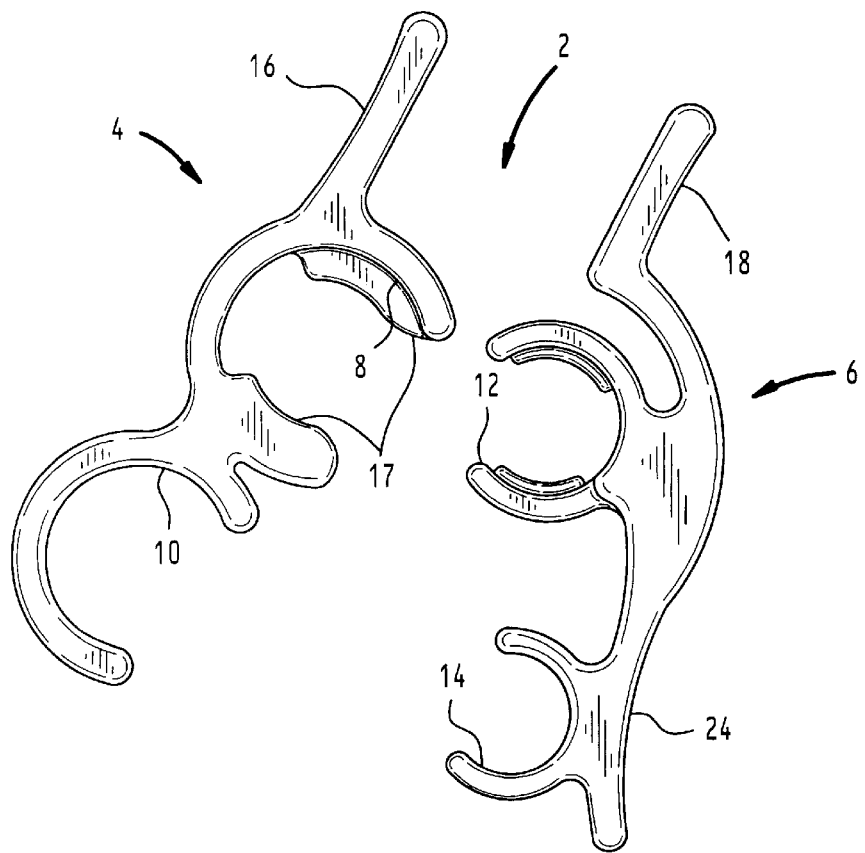
FIGS. 1A and 1B illustrate side and perspective views, respectively, of an unassembled connector constructed in accordance with the principles of the present invention.
Figure 1B:
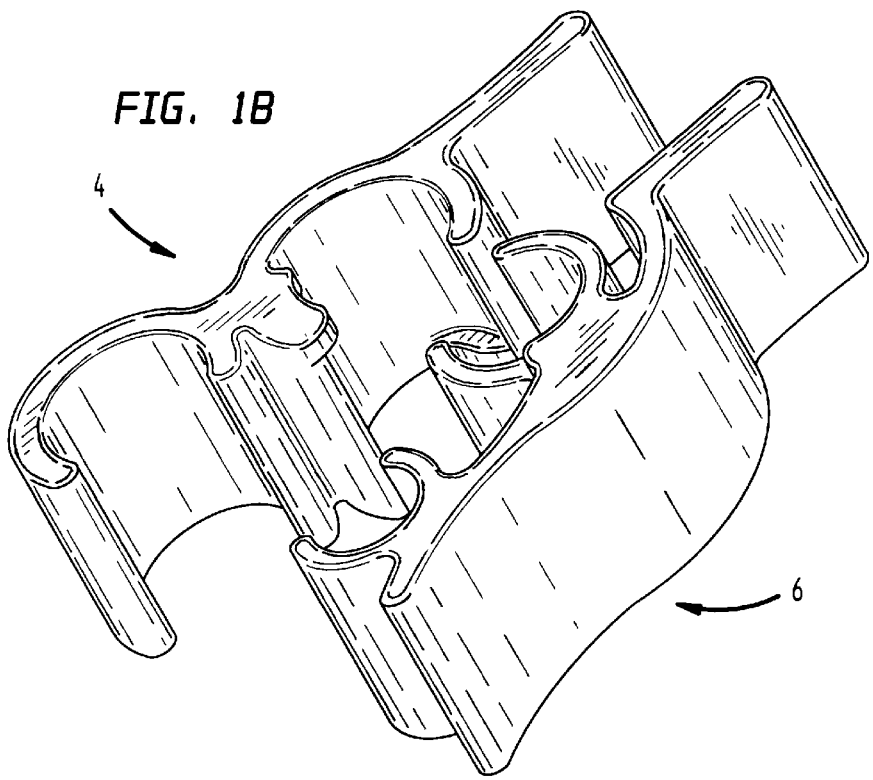

Reference is now made to FIGS. 1A and B which show a side and perspective view, respectively, of an unassembled snap type of fastening device constructed in accordance with the principles of the present invention. Fastening device 2 is composed of first and second complimentary shaped injection molded plastic members 4 and 6. Member 4 includes first and second partial-cylindrical portions 8 and 10 and member 6 includes complimentary shaped first and second partial-cylindrical portions 12 and 14. Portions 8, 12 and 10, 14 are dimensioned so as to form a "snap" type of fit when these portions are urged towards each other so that the partial-cylindrical portions nest or engage one another.

Figure 2A:
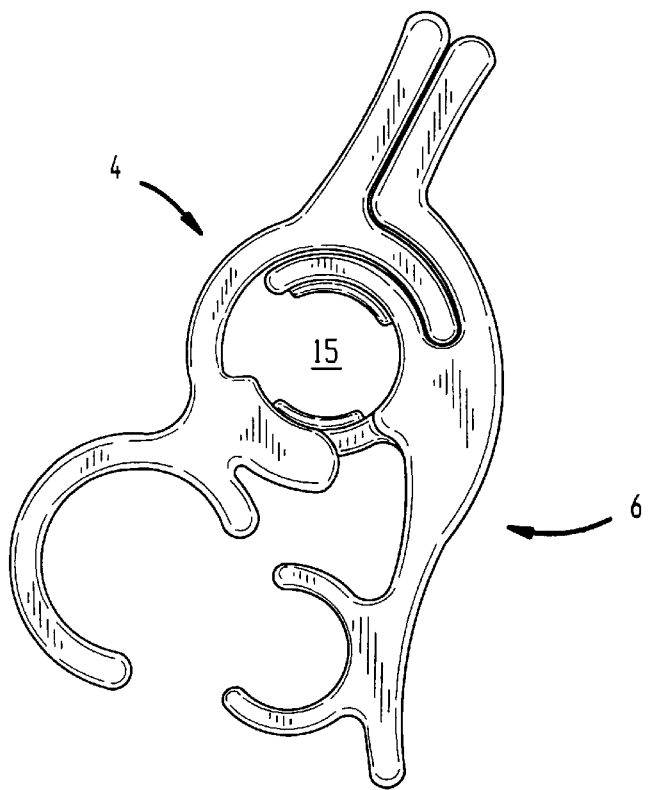
FIGS. 2A and 2B illustrate side and perspective views, respectively, of an assembly connector constructed in accordance with the principles of the present invention.
Figure 2B:
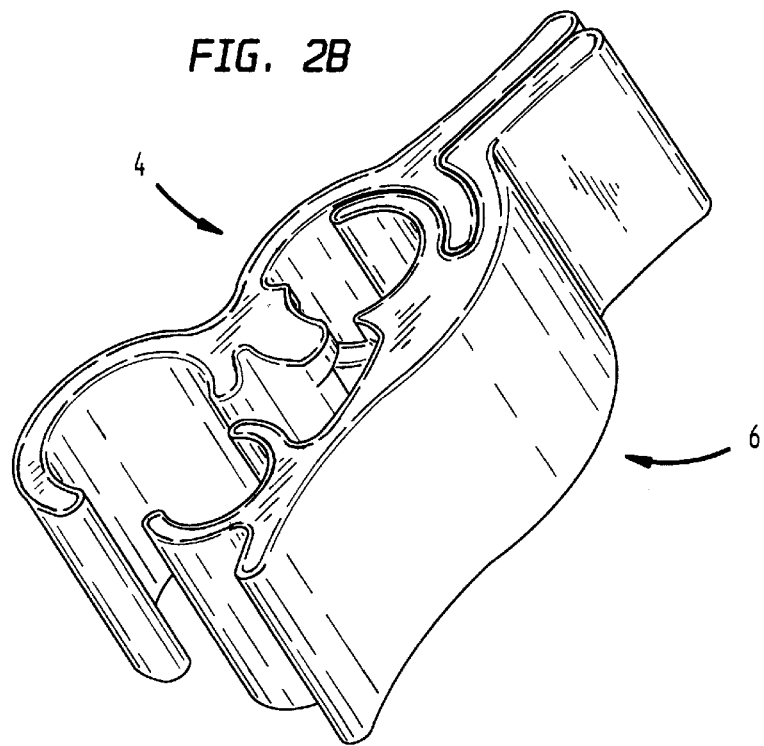

FIGS. 2A and 2B illustrate such an engagement or nesting of portions 8, 12. More specifically, when members 4 and 6 are urged towards each other by a user so that complimentary partial-cylindrical portions 8 and 12 engage each other, portions 8 and 12 form a hinge or pivot 15. Pivot 15 holds members 4 and 6 juxtaposed, while allowing a user of the device to squeeze tab-like portions 16 and 18 which extend from one end of each of members 4 and 6, to cause the opposite ends of members 4 and 6 to assume an "open" position. The opposite ends of members 4 and 6 can also be squeezed by the user of the device so as to cause complimentary partial-cylindrical portions 10 and 14 to engage each other in a snap-like fit in a manner similar to the engagement of portions 8 and 12, and thereby cause fastener 2 to assume a "closed" position. Raised edges 17 (shown more clearly in FIG. 1A) are provided along at least a portion of the outer edges of partial-cylindrical portion 8 so as to prevent longitudinal movement, and disengagement of portions 8 and 12 after they have been engaged.

Due to the shape of partial-cylindrical portions 8, 12 and 10, 14, their selective engagement provides additional functionality to the fastening device.

Figure 3:
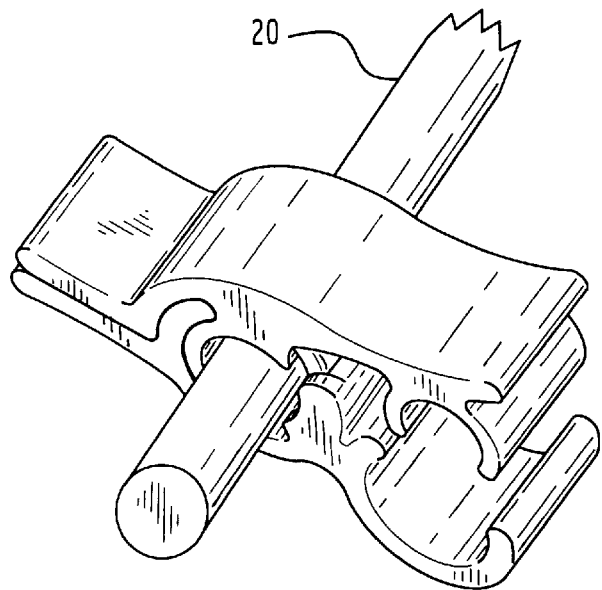
FIG. 3 illustrates the connector of FIG. 1, assembled on an elongate member.

More specifically, FIG. 3 shows assembly of the fastening device 2 upon an elongate member 20 that is secured within the hollow area inside pivot 15 formed by the engagement of complimentary partial-cylindrical portions 8 and 12. Note, the height of the raised edges 17 is dimensioned so as to facilitate a secure (non-slip) pressure engagement of the outside circumference of elongate element 20. Elongate member 20 may comprise, for example, an electrical cable or other tubular element which requires connection to a patient, and at the same time needs attachment to an auxiliary object in order to provide strain relief to the patient.

Furthermore, the fastening device of the present invention allows use of complimentary partial-cylindrical portions 10 and 14 to provide for such attachment of device 2 to an auxiliary object. For example, portions 10, 12 can be used to engage a flexible sheet material (not shown) between the outer curved surface of portion 14 and the inner curved surface of partial-cylindrical portion 10. Due to the fact that these portions are engage for a snap fit, the flexible sheet material can be "pinched" or squeezed thereby, and accordingly securely fasten the elongate member to the sheet material and provide strain relief. The sheet material may comprise, for example, the gown of the patient, a pillowcase, a bed sheet, or other material having a somewhat fixed relation to the patient. Due to the flexible nature of the material used to injection mold members 4 and 6, a variety of different materials and thickness can be "grasped" by the selective engagement of portions 10, 12.

Figure 4:
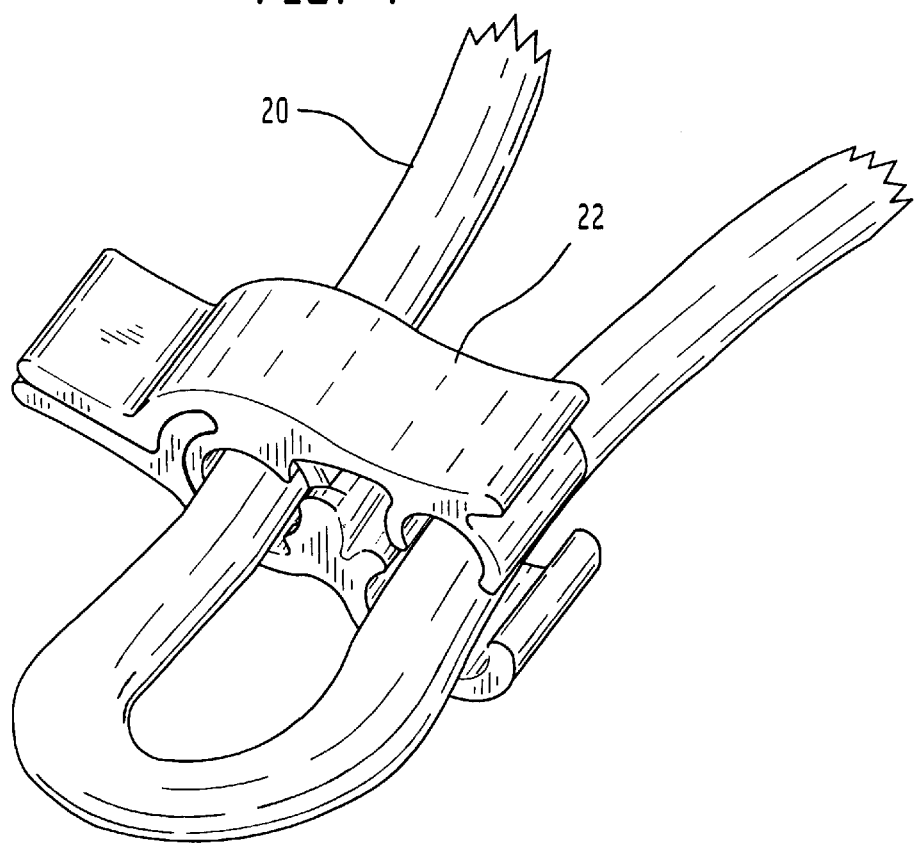
FIG. 4 illustrates the connector of FIG. 3, wherein the elongate member is secured thereby so as to form a loop.

In an alternative use of the present invention, the user could form a loop in the elongate element by folding it back upon itself, and then clamp element 20 within the hollow formed between nested partial-cylindrical complimentary portions 10 and 14, as shown in FIG. 4. This arrangement allows for a variety of possibilities for positioning the elongate element in a somewhat stable and strain-relief position with respect to the patient by, for example, positioning the loop on the hook of an IV pole, or on a portion of the hospital bed.

As previously noted, the selective engaging end of fastening device 2 is opened by the user squeezing together tab-like portions 16 and 18, and conversely, fastener 2 is closed, so as to selectively engage a sheet material or elongate member within portions 10, 14, by squeezing the opposite ends of members 4 and 6 together. For this purpose, as illustrated in FIG. 4, member 6 includes a finger support area 26.

Thus, there has been shown and described a novel apparatus for a snap fastening device. Many changes, modifications, variations and other uses and applications of the subject invention will, however, become apparent to those skilled in the art after considering this specification and its accompanying drawings, which disclose a preferred embodiment thereof. For example, although all of the illustrated partial-cylindrical portions are shown as wall-type (tubular) structures, device 2 would still function if partial-cylindrical portions 12 and 14 were in fact solids. In this case, the engagement of portions 10 and 14 would still provide their "sheet grasping" function, and the engagement of portions 8 and 12 would still provide their "pivot" function. In this case, the shape of device 2 could be modified so as to accommodate an area like engagement area 15 in that portion of member 6 that resides between the outside walls of portions 8 and 10. Additionally, many other variations are possible, i.e., a finger support area that is similar to area 22 could be provided on the complimentary opposed side of member 4. All such changes, modifications, variations and other uses and applications which do not depart from the teachings herein are deemed to be covered by this patent, which is limited only by the claims which follow as interpreted in light of the foregoing description.

What is claimed is:

1. A fastener for engaging an elongate element, comprising:

first and second separable members, each member including first and second complementary shaped partial-cylindrical portions formed on a facing side thereof, wherein the first and second partial-cylindrical portions of the first member have outside dimensions that are complementarily dimensioned with respect to inside dimensions of the first and second partial-cylindrical portions of the second member, so that the first and second partial-cylindrical portions of the first member selectively engage and nest within the first and second partial-cylindrical portions of the second member when the facing side of the first and second members are positioned towards each other, thereby forming a rotatable pivot point for said first and second members when the first partial-cylindrical portions of the first and second members are nested, and wherein the elongate element is engaged between the first and second members of the fastener by an engagement area formed when one of the first and second partial-cylindrical portions are nested.

2. The fastener of claim 1, wherein the first partial-cylindrical portions have a tubular shape so as to form a hollow as said engagement area in the center of the rotatable pivot point.

3. The fastener of claim 2, wherein the first and second members are formed of a flexible plastic material so as to facilitate a snap engagement the first partial-cylindrical portions of the first and second members when they nest.

4. The fastener of claim 1, wherein the second partial-cylindrical portions have a tubular shape so as to form a hollow engagement area therein when they are nested.

5. The fastener of claim 4, wherein the hollow engagement area formed by the nesting of the second partial-cylindrical portions is shaped so as to also engage the elongate element.

6. The fastener of claim 4, wherein the first and second members are formed of a flexible plastic material so as to facilitate a snap engagement the second partial-cylindrical portions of the first and second members when they nest.

7. A fastener for engaging an elongate element, comprising:

first and second separable members, each member including first and second complementary shaped partial-cylindrical wall portions formed on a facing side thereof, wherein the first and second partial-cylindrical wall portions of the first member have outside dimensions that are complementarily dimensioned with respect to inside dimensions of the first and second partial-cylindrical wall portions of the second member, so that the first and second partial-cylindrical portions of the first member selectively engage with a snap fit so as to nest within the first and second partial-cylindrical portions of the second member when the facing side of the first and second members are positioned towards each other, thereby forming a rotatable pivot point for said first and second members, and wherein at least one hollow centered at said rotatable pivot point is created by the nesting of one of the first and second partial-cylindrical portions, said hollow being dimensioned for engaging the elongate element.

8. The fastener of claim 7, said hollow is created in the center of the rotatable pivot point.

9. The fastener of claim 7, wherein the first and second members are formed of a flexible plastic material so as to facilitate a snap engagement of the first partial-cylindrical wall portions of the first and second members when they nest.

10. The fastener of claim 7, wherein first and second hollows are formed by the nesting of the first and second partial-cylindrical wall portions, respectively, both hollows being shaped so as to engage the elongate element.

* * * * *